(12) United States Patent
Willis et al.

(10) Patent No.: US 6,827,738 B2
(45) Date of Patent: Dec. 7, 2004

(54) REFRACTIVE INTRAOCULAR IMPLANT LENS AND METHOD

(76) Inventors: Timothy R. Willis, 1004 Denfield Ct., Raleigh, NC (US) 27615; Lyle E. Paul, 1040 Brentwood Dr., Russell, KY (US) 41169; Joseph Collin, 59 rue de Parc, 33200 Bordeaux (FR)

(*) Notice: Subject to any disclaimer, the term of this patent is extended or adjusted under 35 U.S.C. 154(b) by 0 days.

(21) Appl. No.: 09/774,127

(22) Filed: Jan. 30, 2001

(65) Prior Publication Data

US 2002/0103537 A1 Aug. 1, 2002

(51) Int. Cl.⁷ .................................................. A61F 2/16
(52) U.S. Cl. ..................................... 623/6.43; 623/6.52
(58) Field of Search ............................. 623/6.38, 6.39, 623/6.4, 6.41, 6.43, 6.44–6.55

(56) References Cited

U.S. PATENT DOCUMENTS

| | | |
|---|---|---|
| 3,922,728 A | 12/1975 | Krasnov |
| 3,991,426 A | 11/1976 | Flom et al. |
| 3,996,626 A | 12/1976 | Richards et al. |
| 4,053,953 A | 10/1977 | Flom |
| 4,126,904 A | 11/1978 | Shepard |
| 4,166,292 A | 9/1979 | Anis |
| 4,177,526 A | 12/1979 | Kuppinger |
| 4,206,518 A | 6/1980 | Jardon et al. |
| 4,215,440 A | 8/1980 | Worst |
| 4,304,012 A | 12/1981 | Richard |
| 4,343,050 A | 8/1982 | Kelman |
| 4,535,488 A | 8/1985 | Haddad |
| 4,536,895 A * | 8/1985 | Bittner .................. 623/6.52 |
| 4,575,374 A | 3/1986 | Anis |
| 4,863,462 A | 9/1989 | Fedorov |
| 5,047,052 A | 9/1991 | Dubroff |
| 5,192,319 A * | 3/1993 | Worst .................... 623/6.43 |
| 5,258,025 A | 11/1993 | Fedorov et al. |
| 5,480,428 A | 1/1996 | Fedorov et al. |
| 5,628,796 A | 5/1997 | Suzuki |
| 6,585,768 B2 | 6/1999 | Hamano et al. |
| 5,928,282 A | 7/1999 | Nigam |
| 6,051,024 A | 4/2000 | Cumming |
| 6,152,959 A | 11/2000 | Portnoy |
| 6,228,115 B1 | 5/2001 | Hoffmann et al. |
| 6,478,821 B1 | 11/2002 | Laguette et al. |
| 6,554,860 B2 | 4/2003 | Hoffman et al. |

FOREIGN PATENT DOCUMENTS

WO  WO/92/20302  11/1992  ............ A61F/2/16

OTHER PUBLICATIONS

"Ocular Surgery News", Sep. 1, 2000 5 Pages.

* cited by examiner

*Primary Examiner*—Corrine McDermott
*Assistant Examiner*—Hieu Phan
(74) *Attorney, Agent, or Firm*—Robert G. Rosenthal (57) ABSTRACT

A refractive intraocular lens and method of locating the lens within the eye and attaching the lens to the iris. The refractive intraocular lens may be attached via staples, a fastener or by the tip of the haptics.

12 Claims, 14 Drawing Sheets

SECTION A-A

REFRACTIVE INTRAOCULAR IMPLANT LENS AND METHOD

FIELD OF THE INVENTION

This invention relates generally to the field of intraocular implant lenses and more particularly, to intraocular implant lenses for use in refractive vision correction.

BACKGROUND OF THE INVENTION

It has long been a goal of ophthalmic surgeons to provide patients with alternatives to eyeglasses. Witness the development of the contact lens, radial keratotomy and lasik or laser vision correction surgery. It is estimated that in the year 2000, over two million lasik procedures will be performed. Notwithstanding the popularity of laser surgery, it is not without its drawbacks and deficiencies. For example, recent data has shown that approximately 5–10% of the patients undergoing laser refractive surgery will have suboptimal results such as, a final vision correction which still requires some sort of optical correction or the patient will experience cataract-like "halos". In addition, it has been estimated that up to 50% of the patients post laser surgery experience dry eye symptoms on an ongoing basis.

In response to the foregoing, ophthalmic surgeons have turned to intraocular implant surgery in an effort to advance the art of refractive vision correction. For example, U.S. Pat. No. 5,192,319 to Worst discloses an intraocular refractive lens which is surgically positioned in the anterior chamber and is used in addition to the natural lens to correct for refraction error. The lens comprises an optical portion (the optic) having an inner concave and an outer convex shape. Attached to the outer periphery of the optic is one or more pairs of flexible pincer arms which are adapted to pinch a small portion of the anterior surface of the iris to maintain the implant in place. Notwithstanding the foregoing, the Worst lens has not been widely adopted. This is because the lens requires a hard, non-flexible material to fixate to the iris, thus requiring a large 6 mm or more incision. In addition, the Worst lens is difficult to implant and requires a two handed ambidextrous surgical technique to insert and attach to the iris, skills, which are found in relatively few ophthalmologists.

Other anterior chamber implants have also been attempted without success. For example, U.S. Pat. No. 4,575,374 to Anis discloses an anterior chamber lens comprising an optic and four haptics, each of which flexes independently of the others. U.S. Pat. No. 4,166,293 also to Anis discloses an anterior chamber implant for cataract replacement having an optic and three loops that extend downward and are adapted to fit behind the iris. A fourth loop overlies on of the other loops and overlies the iris when the implant is in place within the eye. The implant is held in place by an attachment member, which connects the fourth loop with the underlying loop by penetrating through the iris. Another anterior chamber implantable lens is disclosed in U.S. Pat. No. 4,177,526 to Kuppinger wherein a pair of opposing arms are attached to the optic. The respective arms are inserted behind the iris and pinch the rear of the iris to hold the implant in place. Another anterior chamber implant lens is disclosed in U.S. Pat. No. 5,047,052 to Dubroff, which teaches an optic, and four haptics extend outwardly therefrom. The haptics are flexible and independently movable. Further, once the implant is inserted and positioned by conventional means, the ends of the haptics are adapted to rest within the optical angle, i.e., the intersection of the cornea and the iris. It is notable that none of the foregoing implant lenses have been widely adopted and in fact only one of the lens (i.e., Worst Lens) is currently in limited use in the European market, as they all experienced surgical or clinical failures including, lens insertion and attachment problems, intraocular or iris bleeding, inflammation, tissue deformation, potential lens induced glaucoma.

Accordingly, it is an object of the present invention to provide an improved refractive implant, which solves the aforementioned problems.

A further object of the present invention is to provide an improved refractive implant, which is minimally surgically invasive.

Another object of the present invention is to provide an improved refractive implant having reduced side-effects, for example dry eyes and inflammation.

An additional object of the present invention is to provide an improved refractive implant, which is easily implantable and removable, if necessary.

A still further object of the present invention is to provide an improved refractive implant, which accurately corrects vision, thus obviating the need for subsequent surgeries.

A correlated object of the present invention is to provide an improved refractive implant, which is easy to manufacture.

Yet another object of the present invention is to provide an improved refractive implant, which does not require expensive equipment, such as lasers.

SUMMARY OF THE INVENTION

In accordance with the present invention, there is provided a refractive intraocular lens that is adapted to be implanted within the eye and which is supported by the iris. The lens is characterized by its ability to be easily inserted and removed with minimal trauma to the eye tissues. The lens comprises an optic for producing a preselected optical effect having an anterior side, a posterior side and an outer peripheral edge. The lens may be foldable or deformable. A haptic is connected to the optic and extends outwardly therefrom. The haptic includes a proximal end, a distal end and an intermediate segment positioned therebetween. The proximal end is connected to the optic and the intermediate segment projects downwardly and away from the posterior side of the optic and the distal end terminates in a pointed tip. The intermediate segment includes a shoulder for supporting the lens on the iris. The distal end of the haptic includes an iris fixation means for attaching the lens to the iris wherein the tip is constructed and arranged to penetrate the iris.

In a second embodiment of the invention, the refractive intraocular lens is attached to the iris by means of a staple, which is adapted to overlie and straddle a portion of the haptic. The staple is compressible from a first relaxed state to a second expanded state such that when the staple is expanded and placed in an overlying straddling relation to the haptic and is released, the staple contracts and attaches the iris, thereby fixing the position of the intraocular lens thereon. Additionally, the staple could be attached to the iris in the reverse manner from that which is described above.

In a third embodiment of the invention, at least one of the haptics includes a hole defining an opening. A fastener is adapted to be received within the opening and to expandingly grip the iris tissue. More specifically, the fastener comprises a shaft having a top end and a bottom end. The bottom end includes includes a flexible barb and the top has a diameter that is greater than the diameter of the opening such that when the fastener is inserted in the opening, the barb is retracted and the fastener slides in the opening and when the barb exits the bottom of the opening, the iris is hooked and the barb becomes embedded therein, thus attaching the intraocular lens to the iris.

BRIEF DESCRIPTION OF THE DRAWINGS

Some of the objects of the invention having been stated, other objects will appear as the description proceeds when taken in connection with the following detailed description and appended claims, and upon reference to the accompanying drawings.

DETAILED DESCRIPTION OF THE PREFERRED EMBODIMENTS

While the present invention will be described more fully hereinafter with reference to the accompanying drawings, in which particular embodiments are shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Figure 1:
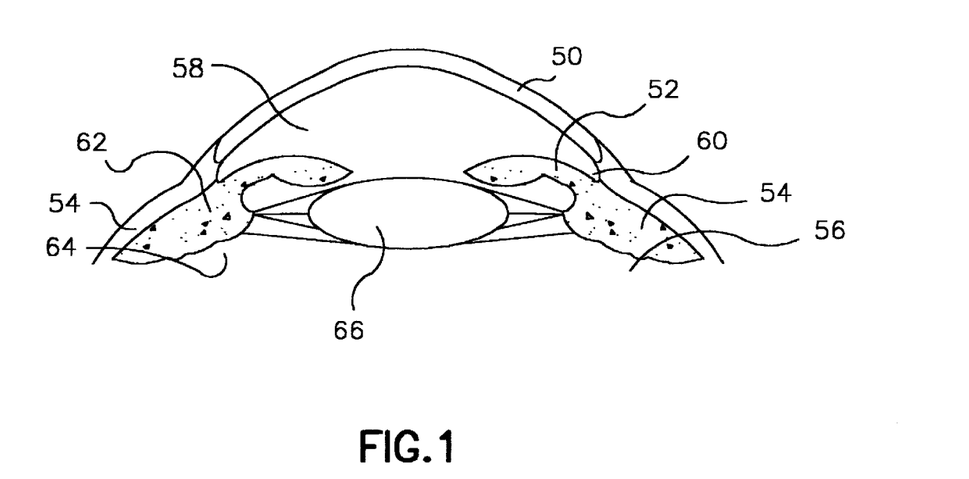
FIG. 1 is a cross section of a human eye.
Figure 2:
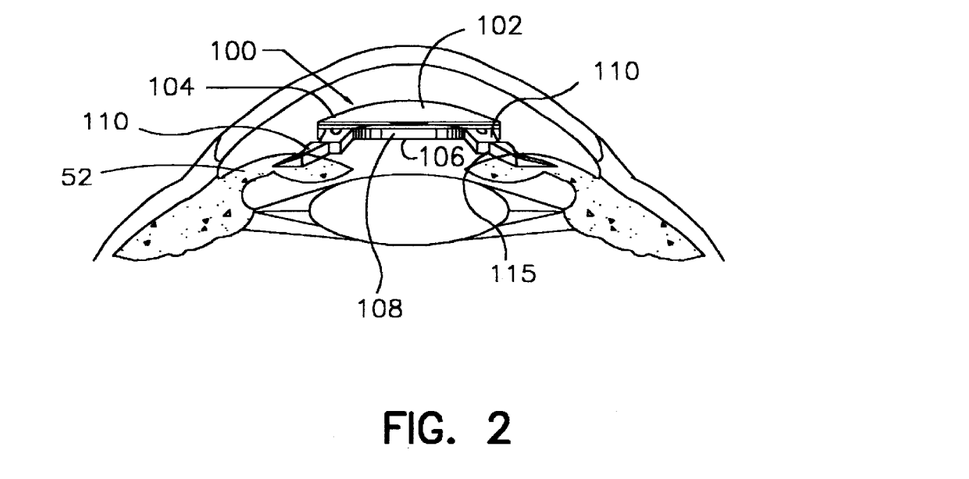
FIG. 2 is a cross section of a human eye with an implant according to the present invention affixed to the iris.
Figure 3:
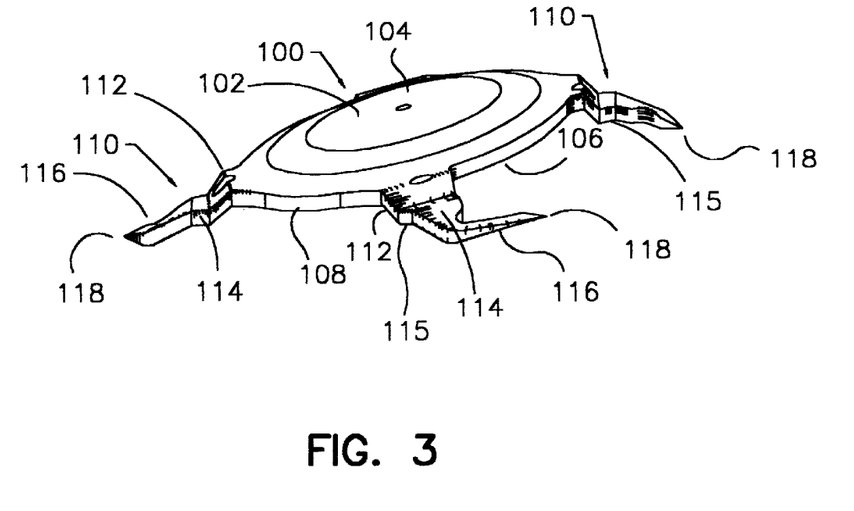
FIG. 3 is a perspective view of an implant lens according to the present invention.
Figure 4:
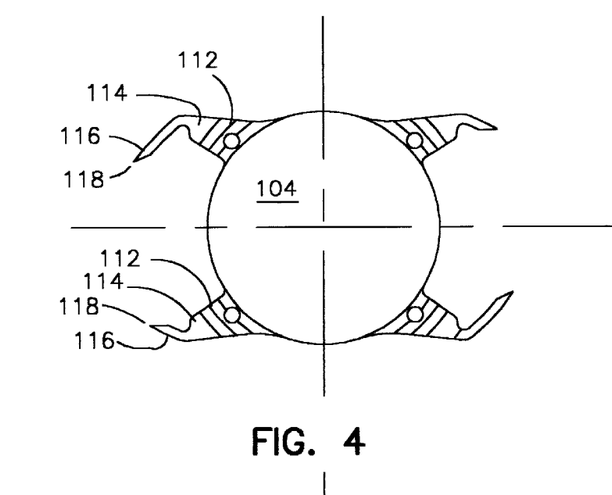
FIG. 4 is a plan view of an implant lens according to the present invention.
Figure 5:
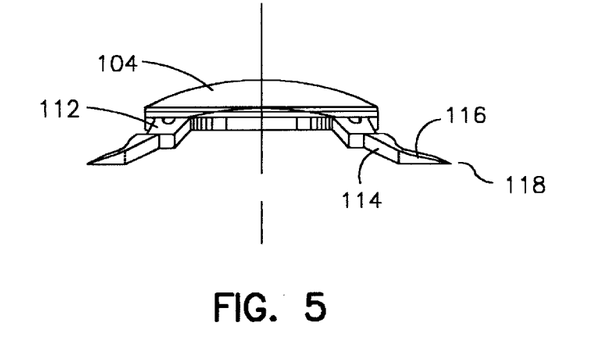
FIG. 5 is an end view of an implant lens according to the present invention.
Figure 6:
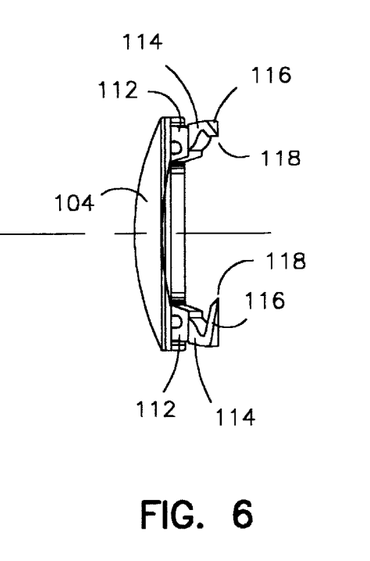
FIG. 6 is an end view of an implant lens according to the present invention.

Referring now to the drawings and particularly to FIG. 1 in which a human eye is schematically illustrated. The structures of the eye include the cornea 50, iris 52, sclera 54, vitreous 56, anterior chamber 58, chamber angle 60, trabecular meshwork 62, posterior chamber 64 and human crystalline lens 66. While the description makes specific reference to the human eye, it will be understood that the invention may be applied to various animals with only minor modifications. For example, mammals such as dogs, cats and horses and the like may suffer injuries when their eyesight deteriorates with age and vision correction surgery as contemplated by this invention may prevent injury and thus extend their useful life.

Turning now to FIGS. 2 through 8, a first embodiment of the invention is there illustrated. The intraocular lens generally indicated at 100 is adapted to be implanted within the eye and includes an optical means or optic 102 and a single or a plurality of haptic means or haptics 110. The optic is generally circular and has an anterior side 104, a posterior side 106 and an outer peripheral edge 108. The diameter of the optic 102 is in the range of approximately 5 mm to 6 mm. In addition, the optic 102 will have varying anterior and posterior curvatures, depending on whether myopia or hyperopia is being corrected. Further curvature variations are added for the correction of cylinder (Astigmatism), presbyopia, bi-focal or multi-focal. The characteristics of the particular optic 102 selected are left to the surgical judgement of the ophthalmologist performing the implant procedure. In addition, the optic 102 and the haptics 110 must be made of a material, which is biologically inert and the optic 102 must additionally be made of a material, which satisfies the necessary optical and surgical insertion requirements. The term "biologically inert" is generally understood in the art to be a material which is not absorbed by the body fluids and which does not cause any adverse reaction when implanted. Commonly used materials alone or in combination for intraocular lenses are silicone, acrylic, collagen, hydrogel and polymethylmethacrylate. Other suitable materials may include ophthalmic glass, quartz and other polymeric materials.

Figure 7:
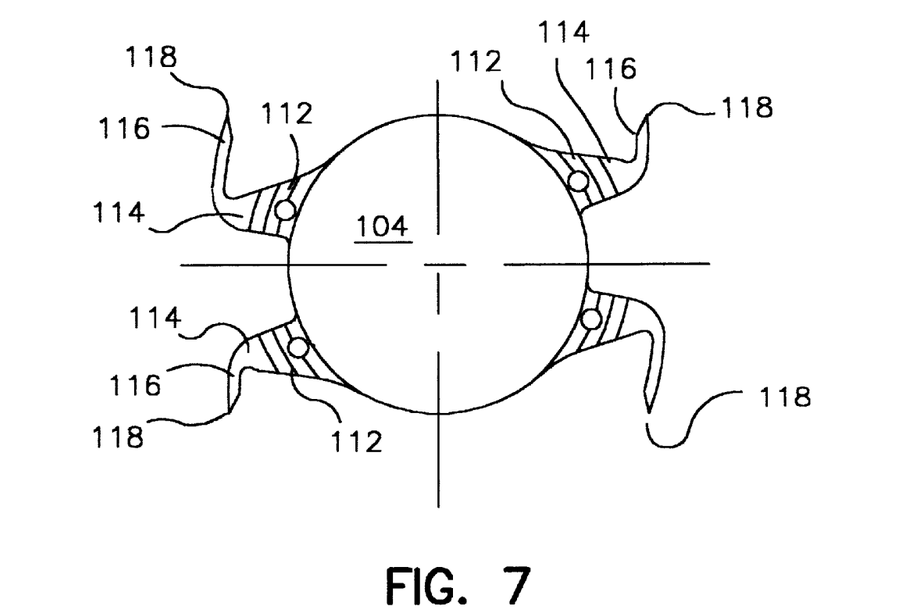
FIG. 7 is a plan view of an implant lens according to the present invention and having a second arrangement of tips.
Figure 8:
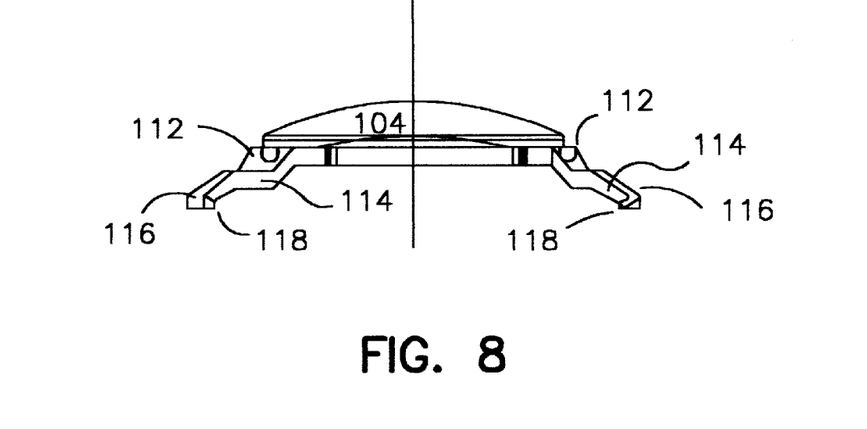
FIG. 8 is an end view of an implant lens according to the present invention and having a second arrangment of tips.
Figure 9:
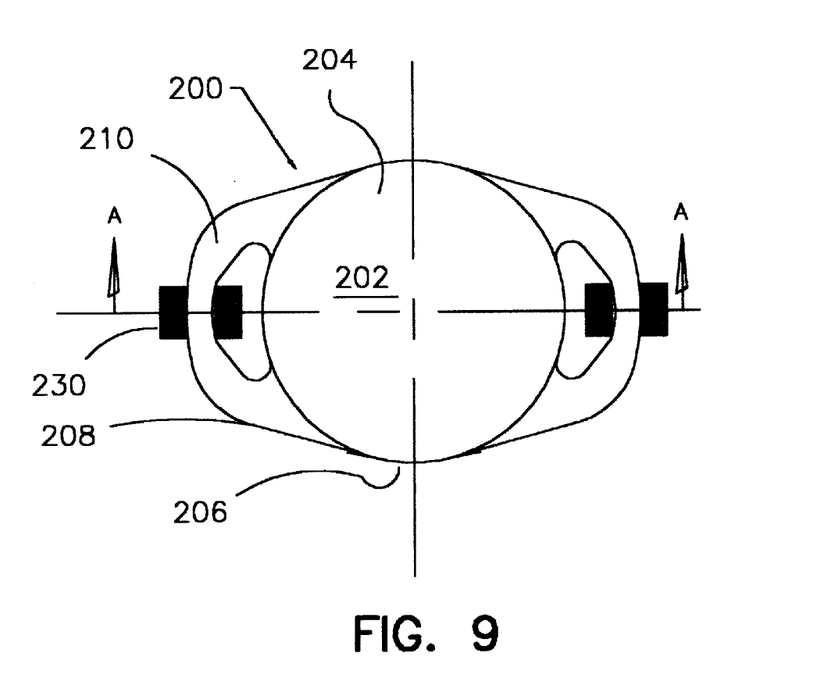
FIG. 9 is a plan view of a second embodiment of the implant lens according to the present invention.
Figure 10:
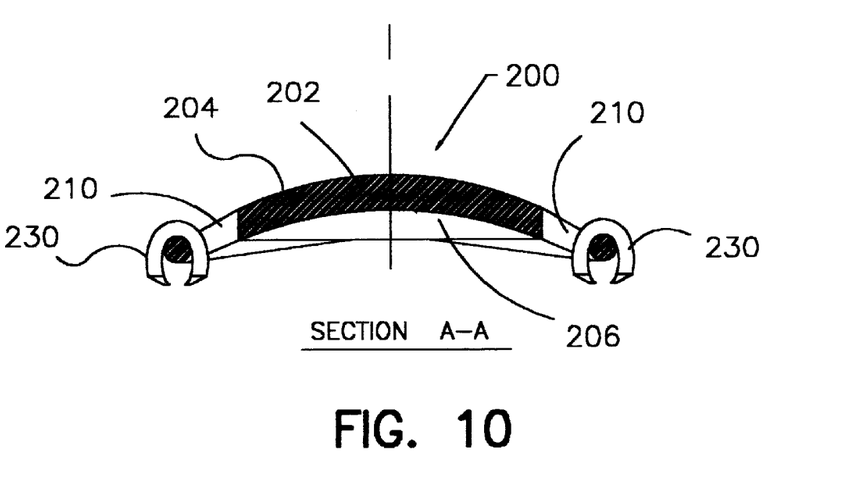
FIG. 10 is a sectional view taken along line A—A of the embodiment of the implant lens of FIG. 9.

A single or a plurality of haptics 110 are connected to the optic 100. The haptics extend outward from the optic and are spaced apart from each other. Each of haptics 110 include a proximal end 112 which is connected to the outer peripheral edge 108 of the optic, an intermediate segment 114, and a distal end 116. The haptics also include a riser means or riser for maintaining the optic in spaced relation from the iris. In the illustrated embodiment, the intermediate segment 114 includes the riser and it projects downwardly and away from the posterior side of the optic 102 in order to "vault" or provide spacing between the underside of the implant and the surface of the iris. In addition, the intermediate segment 114 includes a shoulder 115 which is adapted to support the implant 100 on the surface of the iris 52. The distal end 116 has at it's terminating end, an iris fixation means for attaching the intraocular lens to the iris in the form of a pointed tip 118 which is adapted to penetrate the iris and defines a point of attachment to the iris. In the preferred embodiment, penetration is a portion of, but less than the entire iris, and in the preferred embodiment is approximately one half the thickness of the iris. The amount of penetration will vary with the mass of the implant, the number and structure of haptics and other factors, It will be noted that the haptics are of sufficient length so as to avoid interfering with the muscles that control the opening and closing of the pupil. Alternatively, the staple may be designed such that it pinches, but does not nesessarily penetrate the iris, thereby attaching the intraocular lens. With respect to the embodiment illustrated in FIGS. 2 through 6, four haptics are shown. They are divided into two pairs, each of which extends outwardly and away from the optic at opposite ends thereof. In addition, the respective pointed tips 118 of each pair face inwardly towards each other. The embodiment as shown in FIGS. 7–8 is essentially identical as that just discussed, however the respective pointed tips 118 are in opposing relation or facing outwardly. Either arrangement will adequately anchor the implant 100 on the iris.

In operation, an incision on the order of 4.0 mm is made in the cornea or sclera by the ophthalmic surgeon. Using forceps or intraocular lens insertion instruments, the implant 100 may be folded, deformed or rolled to reduce the overall insertion size, inserted into the eye and centered over the pupillary opening. Each of the haptics is then manipulated such that the tips penetrate the iris. It will be noted that the respective intermediate segments 114 of the haptics 110 include a shoulder portion, which rests on the iris and limits the depth to which the tips 118 can penetrate.

Figure 11:
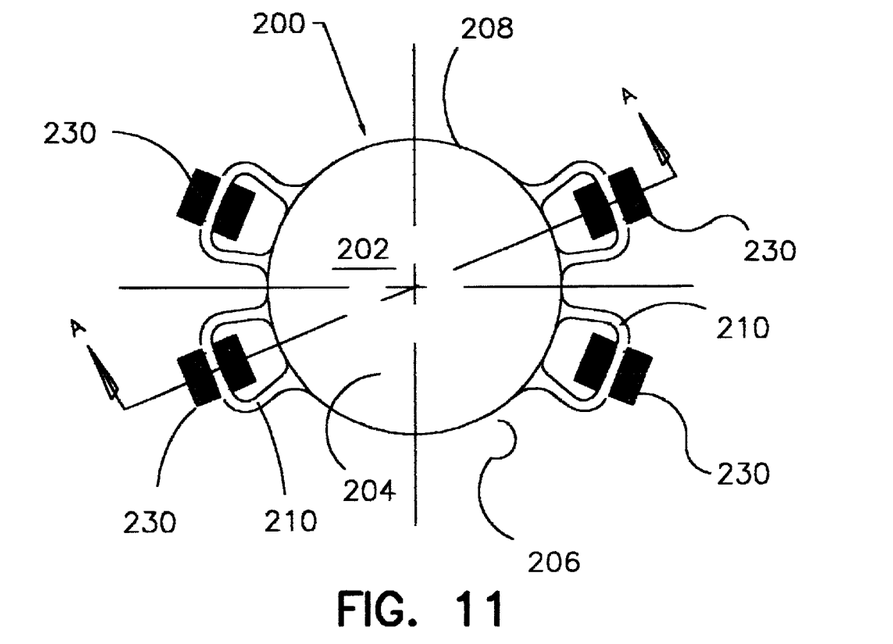
FIG. 11 is a plan view of the second embodiment of the implant lens according to the present invention and having a different haptic arrangment.
Figure 12:
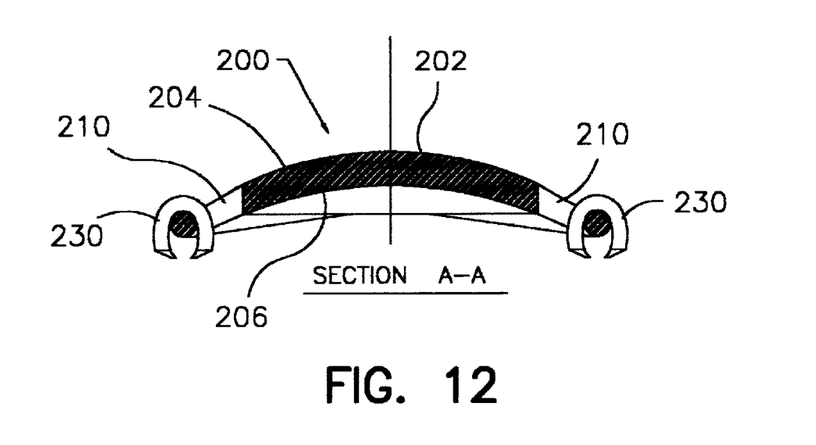
FIG. 12 is a sectional view taken along line A—A of the embodiment of the implant lens of FIG. 11.
Figure 13:
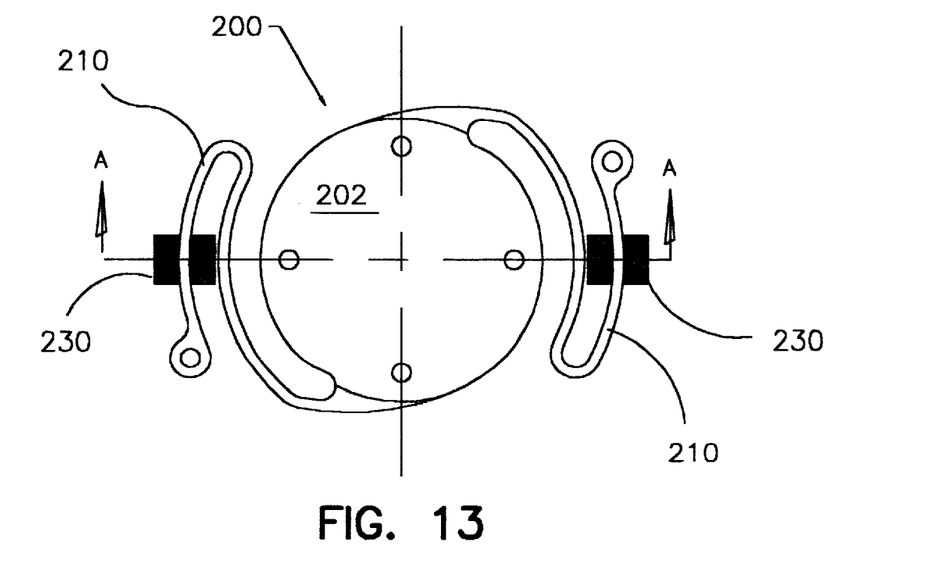
FIG. 13 is a plan view of the second embodiment of the implant lens according to the present invention and having a third haptic arrangment.
Figure 14:
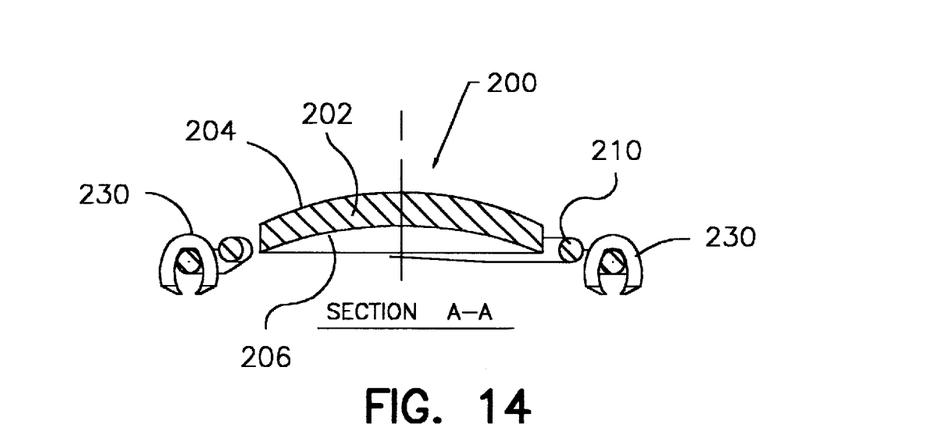
FIG. 14 is a sectional view taken along line A—A of the embodiment of the implant lens of FIG. 13.

A second embodiment of the invention is illustrated in FIGS. 9 through 14 wherein an optical implant 200 is adapted to be implanted within the eye and to be attached to the iris. The implant comprises an optical means or optic 202 for producing a preselected optical effect. The optic 202 has an anterior side 204, a posterior side 206 and an outer peripheral edge 208. A single or plurality of haptic means or haptics 210 are connected to the optic 202. A staple means or staple 230 is adapted to straddle a portion of said haptic 210. The staple 230 is adapted to be manipulated from a relaxed state to a tensioned state whereupon it is released and and attaches to the iris. In the illustrated embodiment, the staple in the relaxed state is expanded. It is then compressed (with an insertion tool discussed hereinbelow), placed in overlying straddling relation to the respective haptic(s), and upon release, expands to substanitally return to its original state, thereby fixing the position of the optical implant thereon. It will be noted that the tensioned and relaxed states could be reversed with equal effacacy. As with the embodiment shown in FIGS. 9–14, the staple is dimensioned such that it penetrates a portion of, but less than the entire iris, preferably, approximately one-half the thickness of the iris. The reader will appreciate that the dimensions and degree of iris penetration will vary with the particular type of optical implant used. For example, in FIGS. 9 and 10, optical implants having a pair of vaulted loop-type haptics located on opposite sides of the optic is shown with staples. In FIGS. 11–12 an optical implant having four vaulted loop-type haptics is shown with staples. Further, the haptics are configured such that the optic is in spaced relation from the iris. In FIGS. 13–14 an optical implant with flexible curved haptics is shown with staples 230. In this embodiment, the staple(s) could be located such that the intraocular lens expands and contracts with the dilation of the iris sphincter muscle.

Figure 19:
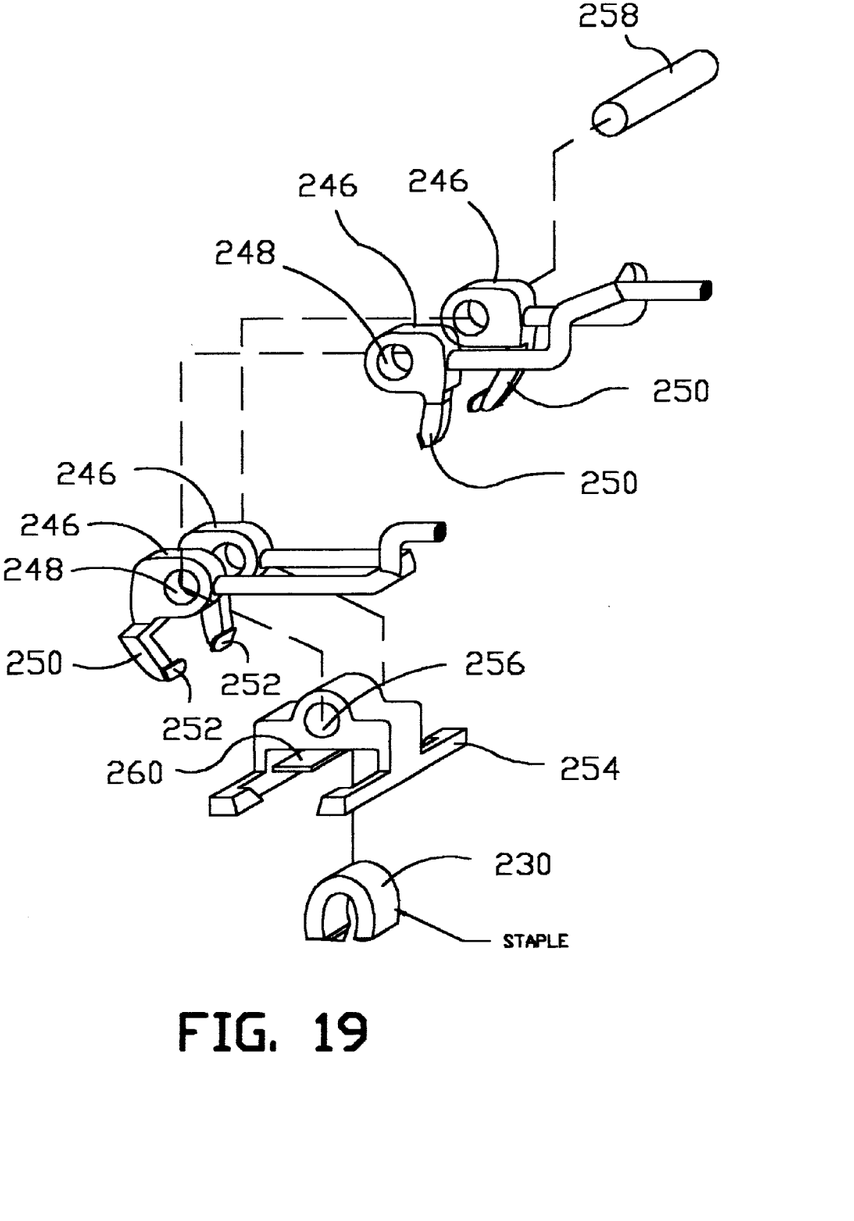
FIG. 19 is an exploded view of the staple insertion tool according to the present invention.
Figure 20:
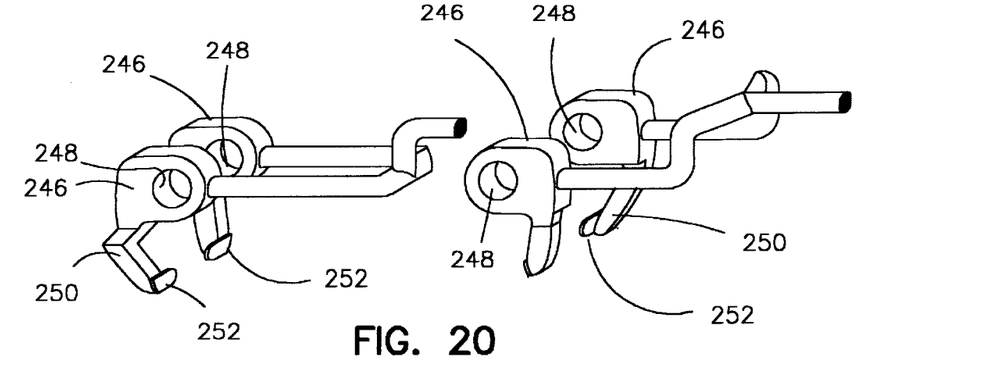
FIG. 20 is a perspective view of a portion of the staple insertion tool according to the present invention.
Figure 21:
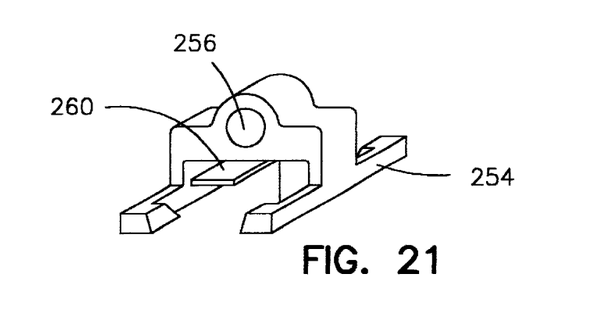
FIG. 21 is a perspective view of the trap lock and gripping fingers portion of the staple insertion tool according to the present invention.
Figure 22:
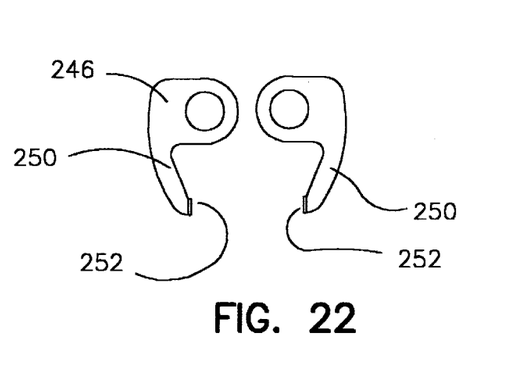
FIG. 22 is a side view of the gripping fingers portion of the staple insertion tool in the open staple releasing position.
Figure 23:
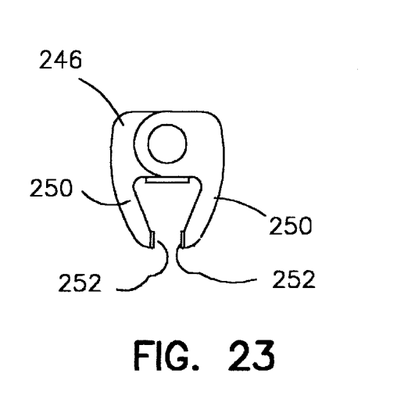
FIG. 23 is a side view of the gripping fingers portion of the staple insertion tool in the closed staple gripping position.
Figure 24:
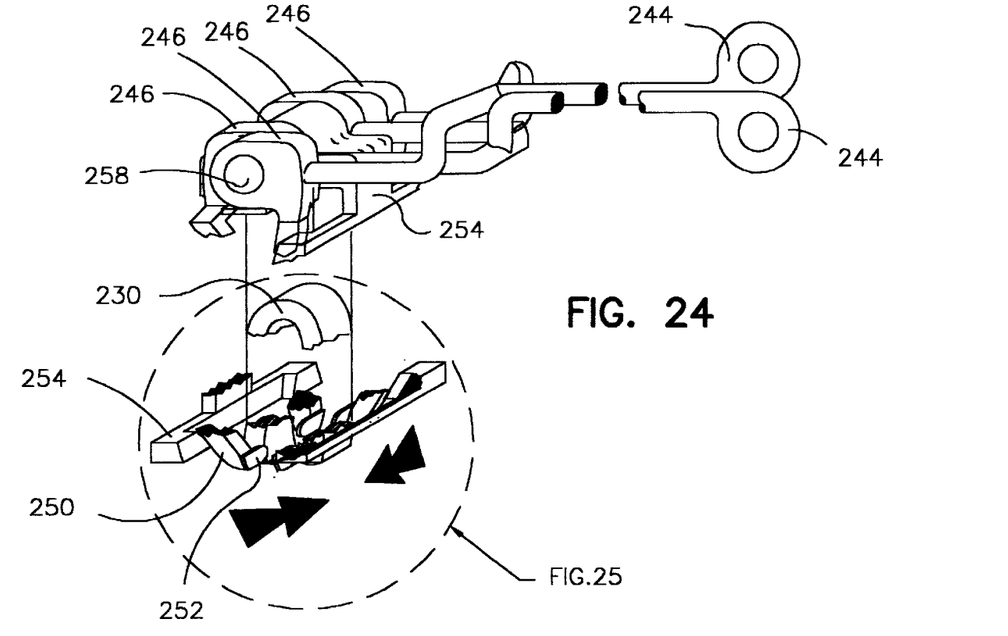
FIG. 24 is a perspective view of the staple insertion tool according to the present invention in the closed staple gripping mode.
Figure 25:
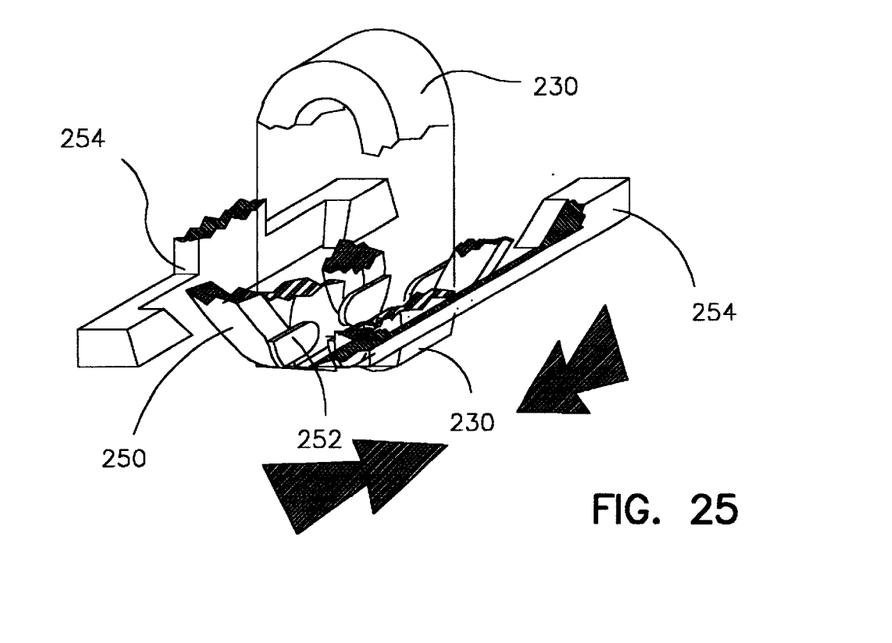
FIG. 25 is a detailed perspective view, partially broken away, of the gripping portion of the tool as illustrated in FIG. 24.
Figure 26:
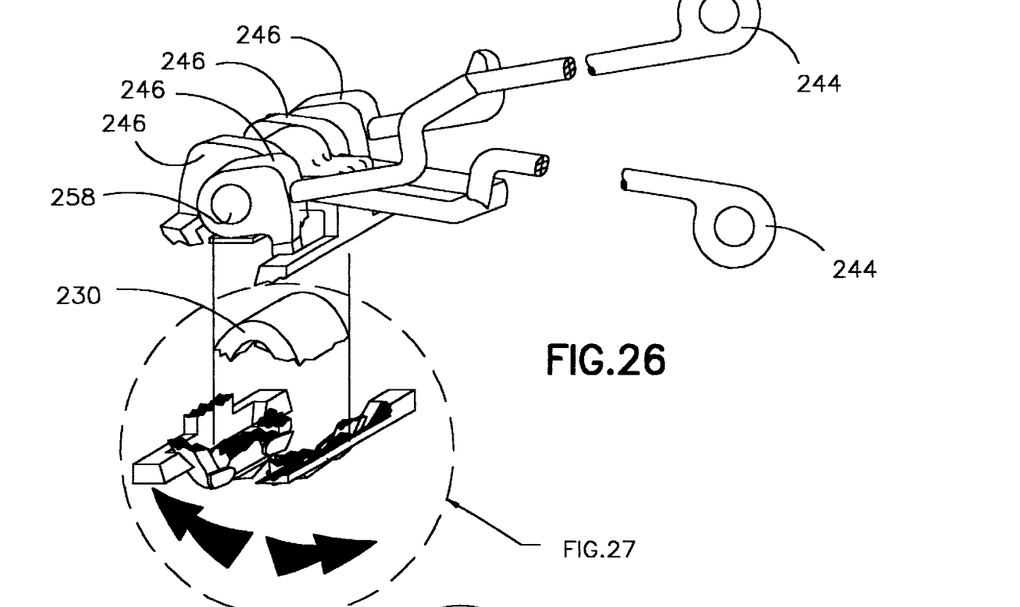
FIG. 26 is a perspective view of the staple insertion tool according to the present invention in the open staple releasing mode.
Figure 27:
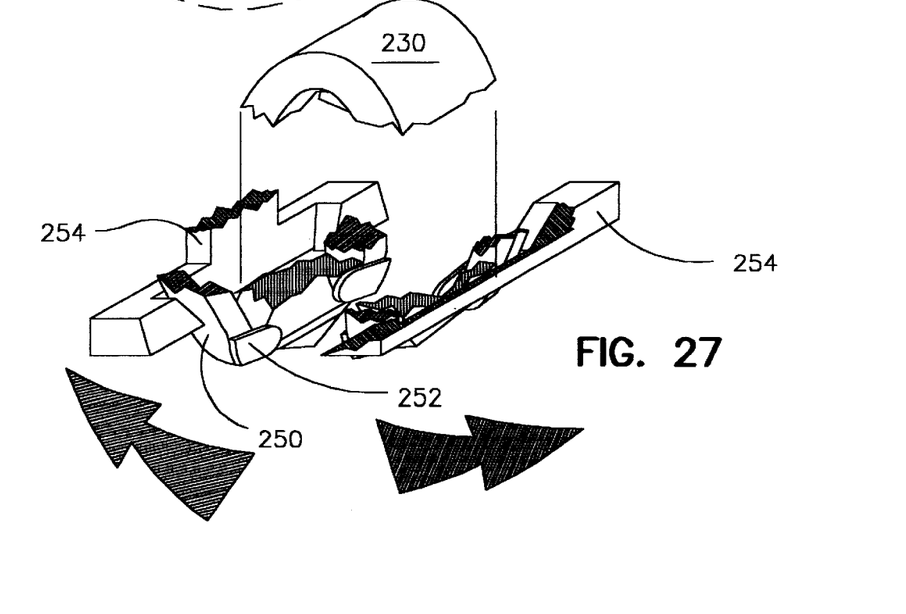
FIG. 27 is a detailed perspective view, partially broken away, of the gripping portion of the tool as illustrated in FIG. 26

The staples 230 employed in the above-noted embodiment are inserted using an insertion instrument generally indicated at 240 as illustrated in FIGS. 18 through 27. It will be noted that prior to insertion, the staple must be transported by the surgeon within the eye, and further, that once within the eye, is not susceptible to adjustment. Thus, the instrument, which is described in detail hereinbelow, is designed with safety features such that it is difficult to accidentally release the staple and further, once released, the staple automatically contrats and grippingly attaches to the iris. With the foregoing in mind, the instrument comprises a pair of manipulating rods or handles 242 having respective finger loops 244 at one end which assist the surgeon in one-handed operation during insertion of the instrument tip into the eye. The opposite ends of the respective handles divide into a U shaped bracket, which supports a block 246. In the center of the block 246 is a hole defining an opening 248. A finger 250 depends downward and inward and terminates in a gripping tab 252. Also provided is a locking plate 254 which includes a U-shaped block having an elongate bore 256 therein which allows it to be placed in alignment with the other blocks 246 when pivot pin 258 is aligned therein. A rectangular plate 260 is attached to the underside of the block as best shown in FIG. 19. The plate 260 establishes the limit of vertical travel staple 230 in the instrument.

In operation, the instrument handles are spread apart to spread the fingers 250 and locking plates 254. The staple 230 is then inserted such that the arched mid-section abuts plate 260 and the legs are situated between opposing pairs of gripping tabs 252. The handles are then moved together which causes the staple to be caught between locking plate 254, gripping tabs 252 and plate 260. Continued pressure causes the staples opening to become expanded. The instrument is then inserted in the eye such that the staples overlies in straddling relation the haptic. The manipulating rods are then moved apart from each other which causes the locking plate 254 to move outward, which in turn permits the staple 230 to slide out from between the gripping fingers and to contract into the iris.

Figure 15:
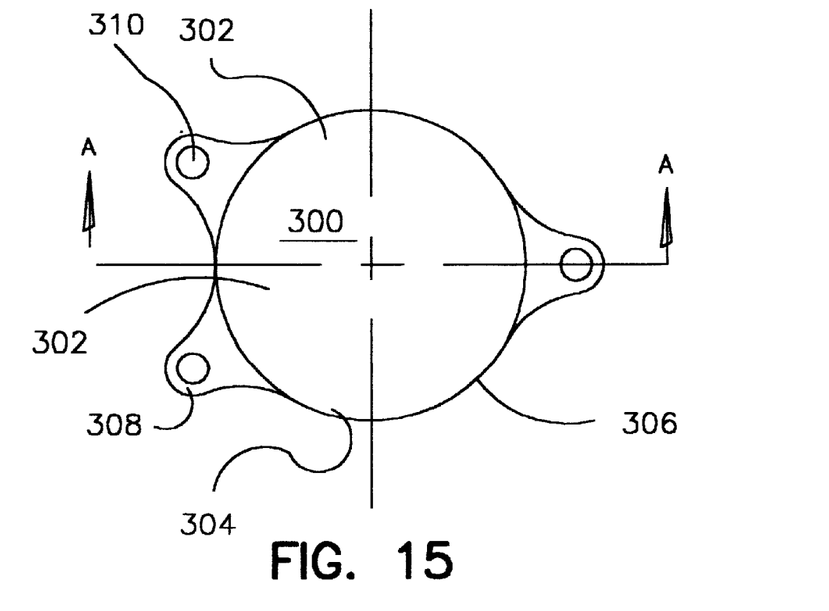
FIG. 15 is a plan view of a third embodiment of the implant lens according to the present invention.
Figure 16:
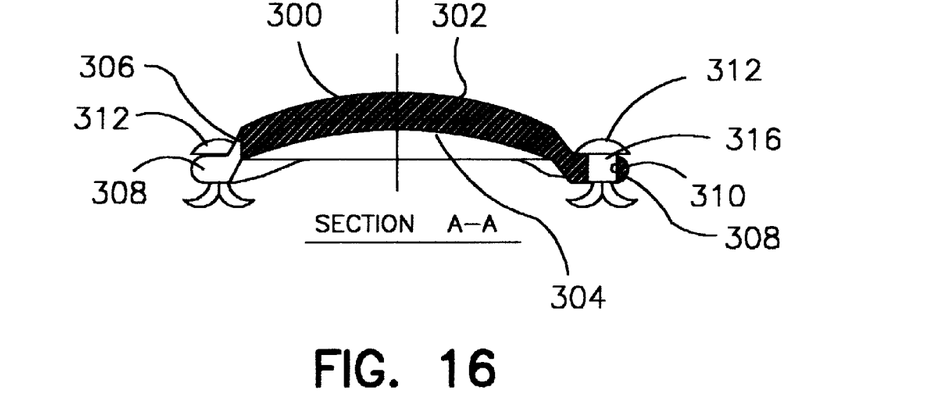
FIG. 16 is a sectional view taken along line A—A of FIG. 15 of the implant lens according to the present invention.
Figure 17:
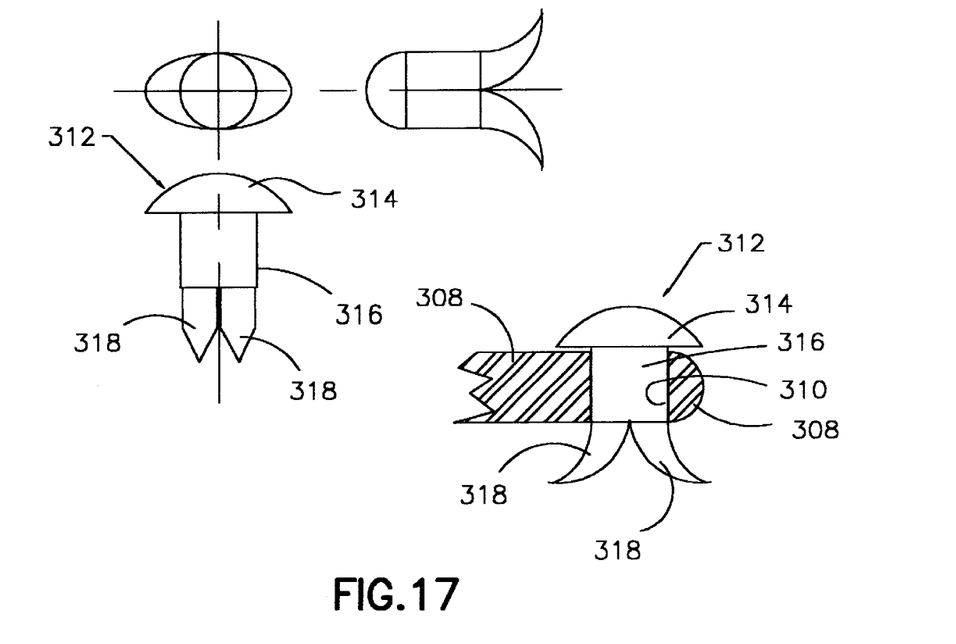
FIG. 17 is a side view of the fastening means according to the present invention being pushed downward through the haptic and into the iris.
Figure 18:
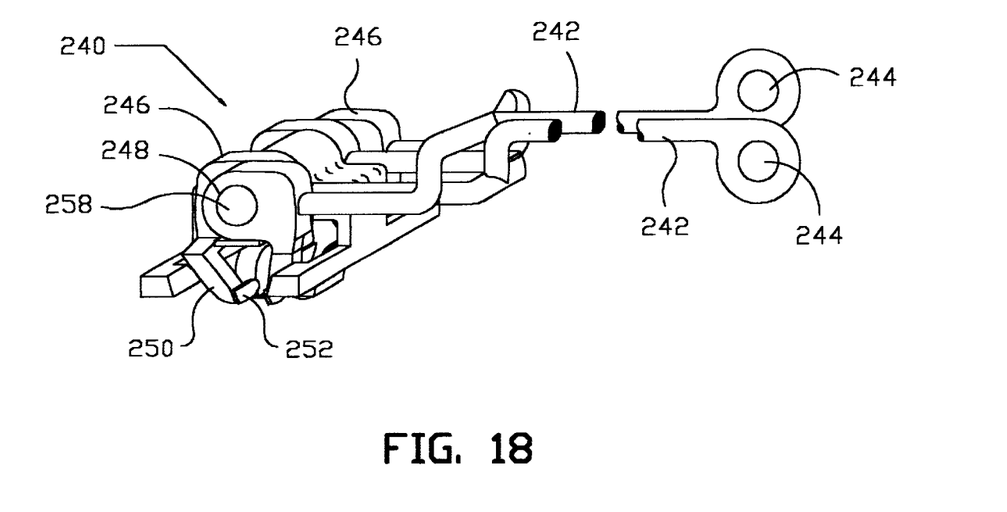
FIG. 18 is a perspective view of the staple insertion tool according to the present invention.

A third embodiment of the invention is illustrated in FIGS. 15 through 17. In that embodiment an optical means or implant 300 for producing a preselected optical effect on light entering the eye and adapted to be implanted in overlying relation to the iris 52 is employed. The implant 300 includes an anterior side 302 and a posterior side 304 and an outer peripheral edge 306. A single or plurality of haptic means or haptics 308 are connected to the implant 300 such that at least one includes a hole defining an opening 310. A fastening means 312 for fixing the position of the intraocular lens on the iris is provided.

The fastening means or fastener 312 is adapted to be inserted within the opening 310 and to expandingly grip the iris tissue. More specifically, the fastening means 312 comprises a shaft having a top end 314 and a bottom end 316. Located at the bottom end 316 is a flexible barb 318 and the top end 314 has a diameter that is greater than the diameter of opening 310. As illustrated in FIG. 17, the barbs are arranged to point outwardly when relaxed.

In operation, the implant 300 is centered over the iris. Then fastener 312 is gripped with forceps (not shown) such that the barbs 318 are compressed. The fastener 312 is then guided into the opening 310 and downward pressure is then gently exerted to push the staple 312 through opening 310. As the barbs exit the opening on the anterior side 304, they contact the iris tissue and begin to expand. When the top end 314 contacts the upper surface of the haptic 308, the barbs penetrate the iris (approximately one-half of the thickness of the iris in the illustrated embodiment) and the position of the implant 300 is fixed in the eye. The foregoing procedure is repeated for each haptic and the number of fasteners employed will depend on the geometry of the specific implant 300 chosen by the surgeon.

The present invention, of course may be carried out in other specific ways than those herein set forth without departing from the spirit and essential characteristics of the invention. The present invention is therefor, to be considered in all respects as illustrative and not restrictive, and all changes coming within the meaning and range of the appended claims are intended to be embraced therein.

That which is claimed is:

1. An intraocular lens adapted to be inserted and fixated in the eye, the intraocular lens being characterized by its ability to be easily inserted and removed with minimal trauma to the eye tissues, and comprising:

an optic for producing a preselected optical effect, said optic having an anterior side, a posterior side and an outer peripheral edge;

a plurality of flexible haptics connected to said optic, said haptics extending outward from said optic and being spaced apart from each other, and wherein at least one of said haptics includes a proximal end and a distal end, said proximal end being connected to said optic and said distal end terminating in a pointed tip adapted to penetrate at least a portion of the iris and further, wherein said haptic includes a riser means for maintaining said optic in spaced relation from the iris;

whereby the intraocular lens may be easily implanted in the eye upon penetration of the fixation means into the iris.

2. An intraocular lens according to claim 1 wherein said haptic includes an intermediate segment positioned between the proximal end and the distal end and wherein the intermediate segment includes a shoulder means for supporting the intraocular lens on the iris.

3. The intraocular lens according to claim 1 wherein said pointed tip is constructed and arranged to penetrate about one half the thickness of the iris.

4. The intraocular lens according to claim 1 further including two pairs of haptics extending oppositely from said optic and wherein said respective distal ends of each pair extend inwardly in a facing relation.

5. The intraocular lens according to claim 1 wherein the optic is foldable, whereby the intraocular lens may be inserted with small incision techniques which, cause less trauma to the eye tissues.

6. An intraocular lens adapted to be inserted and fixated in the eye, the intraocular lens being characterized by its ability to be easily inserted and removed with minimal trauma to the eye tissues, and comprising:

an optic for producing a preselected optical effect, said optic having an anterior side, a posterior side and an outer peripheral edge;

a haptic connected to said optic, said haptic extending outward from said optic and including an iris fixation means for attaching the intraocular lens to the iris, and further wherein said iris fixation means terminates in a pointed tip that defines a point of attachment to the iris such that the tip penetrates at least a portion of, but less than the entire thickness of the iris;

whereby the intraocular lens may be easily implanted in the eye upon penetration of the fixation means into the iris.

7. An intraocular lens according to claim 6 further including a plurality of flexible haptics connected to said optic, each of said haptics extending outward from said optic and being spaced apart from each other, and wherein at least one of said haptics includes a a proximal end and a distal end, said proximal end being connected to said optic, said distal end terminating in a pointed tip adapted to penetrate at least a portion of the iris and further wherein said haptic means includes a riser means for maintaining said optic in spaced relation from the iris;

whereby the intraocular lens may be easily implanted in the eye upon penetration of the haptic means tip into the iris.

8. An intraocular lens according to claim 7 wherein said haptic includes an intermediate segment positioned between the proximal end and the distal end and wherein the intermediate segment includes a shoulder means for supporting the intraocular lens on the iris.

9. The intraocular lens according to claim 6 wherein said iris fixation means is constructed and arranged to penetrate about one half the thickness of the iris.

10. The intraocular lens according to claim 6 further including two pairs of haptics extending oppositely from said and wherein said respective distal ends of each pair extend inwardly in a facing relation.

11. The intraocular lens according to claim 6 further including two pairs of haptics extending oppositely from said optic and wherein the respective distal ends of each pair extend outwardly away from each other.

12. The intraocular lens according to claim 6 wherein the optic is foldable, whereby the intraocular lens may be inserted with small incision techniques which, cause less trauma to the eye tissues.

* * * * *